United States Patent
Takii

(10) Patent No.: US 9,655,507 B2
(45) Date of Patent: May 23, 2017

(54) CORNEAL IMAGING DEVICE

(71) Applicant: NIDEK CO., LTD., Gamagori-shi, Aichi (JP)

(72) Inventor: Michihiro Takii, Nukata-gun (JP)

(73) Assignee: NIDEK CO., LTD., Gamagori-shi (JP)

( * ) Notice: Subject to any disclaimer, the term of this patent is extended or adjusted under 35 U.S.C. 154(b) by 150 days.

(21) Appl. No.: 14/354,375

(22) PCT Filed: Nov. 1, 2012

(86) PCT No.: PCT/JP2012/078397
§ 371 (c)(1),
(2) Date: Apr. 25, 2014

(87) PCT Pub. No.: WO2013/065805
PCT Pub. Date: May 10, 2013

(65) Prior Publication Data
US 2014/0293033 A1    Oct. 2, 2014

(30) Foreign Application Priority Data
Nov. 2, 2011  (JP) ................... 2011-241722

(51) Int. Cl.
*A61B 3/00*    (2006.01)
*H04N 5/225*   (2006.01)
(Continued)

(52) U.S. Cl.
CPC .............. *A61B 3/0008* (2013.01); *A61B 3/12* (2013.01); *A61B 3/14* (2013.01); *A61B 3/152* (2013.01); *A61B 3/156* (2013.01); *H04N 5/2256* (2013.01)

(58) Field of Classification Search
None
See application file for complete search history.

(56) References Cited

U.S. PATENT DOCUMENTS 3,864,030 A * 2/1975 Cornsweet ............ A61B 3/113
                                                           351/210
5,031,623 A * 7/1991 Kohayakawa ........ A61B 3/165
                                                           600/401
(Continued)

FOREIGN PATENT DOCUMENTS

EP    1 723 903 A1    11/2006
EP    2 090 221 A1     8/2009
(Continued)

OTHER PUBLICATIONS

International Search Report issued in International Application No. PCT/JP2012/078397 dated Jan. 22, 2013.
(Continued)

*Primary Examiner* — Mohammad J Rahman
(74) *Attorney, Agent, or Firm* — Oliff PLC

(57) ABSTRACT

A corneal imaging device provided with an optical system for photographing a corneal portion of an eye, the optical system including an illumination optical system configured to irradiate illumination light toward a cornea and a light receiving optical system placed in a position inclined with respect to an optical axis of the illumination optical system configured to receive reflection light from the cornea by a photodetector, wherein the corneal imaging device includes light-limiting means provided in an optical path of the optical system for photographing the corneal portion of the eye and configured to limit light asymmetrically with respect to an optical axis.

9 Claims, 4 Drawing Sheets

(51) Int. Cl.
*A61B 3/12* (2006.01)
*A61B 3/14* (2006.01)
*A61B 3/15* (2006.01)

(56) References Cited

U.S. PATENT DOCUMENTS

| | | | | |
|---|---|---|---|---|
| 5,042,940 A * | 8/1991 | Iwamoto | A61B 3/152 | 351/208 |
| 5,054,907 A * | 10/1991 | Sklar | G01B 11/2513 | 351/212 |
| 5,258,791 A * | 11/1993 | Penney | A61B 3/14 | 351/208 |
| 5,436,679 A * | 7/1995 | Ohtsuka | A61B 3/145 | 351/206 |
| 5,941,250 A * | 8/1999 | Aramant | A61F 9/00727 | 128/898 |
| 6,072,623 A * | 6/2000 | Kitajima | A61B 3/135 | 351/221 |
| 7,572,010 B2 * | 8/2009 | Nishio | A61B 3/145 | 351/205 |
| 9,039,176 B2 * | 5/2015 | Honda | A61B 3/152 | 351/206 |
| 2003/0137669 A1 * | 7/2003 | Rollins | G01N 21/4795 | 356/479 |
| 2004/0135969 A1 * | 7/2004 | Hanebuchi | A61B 3/103 | 351/212 |
| 2007/0146632 A1 * | 6/2007 | Chipman | A61B 3/12 | 351/205 |
| 2008/0239065 A1 * | 10/2008 | Momonoi | G02B 27/2214 | 348/49 |
| 2009/0163898 A1 * | 6/2009 | Gertner | A61B 3/113 | 606/4 |
| 2009/0244483 A1 * | 10/2009 | Yoshino | A61B 3/14 | 351/206 |
| 2010/0014052 A1 * | 1/2010 | Koschmieder | G02B 17/0621 | 351/207 |

FOREIGN PATENT DOCUMENTS

| | | |
|---|---|---|
| EP | 2 095 761 A1 | 9/2009 |
| GB | 2 294 543 A | 5/1996 |
| JP | A-5-123295 | 5/1993 |
| JP | A-8-117189 | 5/1996 |
| JP | A-8-206080 | 8/1996 |
| JP | H09-56675 A | 3/1997 |

OTHER PUBLICATIONS

Jun. 29, 2015 extended Search Report issued in European Patent Application No. 12845173.9.

* cited by examiner

CORNEAL IMAGING DEVICE

CROSS-REFERENCE TO RELATED APPLICATIONS

This is a US national phase application based on the PCT International Patent Application No. PCT/JP2012/078397 filed on Nov. 1, 2012, and claiming the priority of Japanese Patent Application No. 2011-241722, filed on Nov. 2, 2011, the entire contents of which are herewith incorporated by reference.

TECHNICAL FIELD

The present invention relates to a corneal imaging device for imaging an image of a corneal portion of an examinee's eye.

BACKGROUND ART

As a corneal imaging device, for example, there is known a device configured to irradiate illumination light toward a cornea from an illumination light source, and receive reflection light from the cornea through an imaging element to obtain a cell image of a corneal endothelium in non-contact with the cornea (see Patent Document 1).

RELATED ART DOCUMENTS

Patent Documents

Patent Document 1: JP-A-8(1996)-206080

SUMMARY OF INVENTION

Problems to be Solved by the Invention

Meanwhile, conventionally, a circular diaphragm or a rectangular diaphragm is placed symmetrically with respect to an optical axis of an optical system. According to analysis of the present inventor, however, the above corneal imaging device is an optical system having a special object surface for observing an object from an oblique direction and therefore it is found that aberration causes a part of light having passed through a peripheral part of a lens to adversely affect image formation (imaging), contributing to deterioration in quality of an image. In a case where the circular diaphragm or the rectangular diaphragm is designed with an aperture having a simply reduced diameter, the influence of aberration is decreased, whereas a resultant image gets dark, which leads to lowering of resolving power.

The present invention has a purpose in view of the above problems to provide a corneal endothelial cell imaging device capable of ensuring brightness and resolving power of an image, and acquiring an endothelial image suitable for observation and analysis.

Means of Solving the Problems

To achieve the above purpose, the invention provides the following configurations.

One aspect of the invention provides a corneal imaging device provided with an optical system for photographing a corneal portion of an eye, the optical system including an illumination optical system configured to irradiate illumination light toward a cornea and a light receiving optical system placed in a position inclined with respect to an optical axis of the illumination optical system configured to receive reflection light from the cornea by a photodetector, wherein the corneal imaging device includes light-limiting part provided in an optical path of the optical system for photographing the corneal portion of the eye and configured to limit light asymmetrically with respect to an optical axis.

MODE FOR CARRYING OUT THE INVENTION

<Brief Summary>

A device of an embodiment of the present invention relates to a device for photographing an image of a corneal portion of an examinee's eye and is provided with an optical system for photographing or imaging a corneal portion of an eye in non-contact therewith, the optical system including an illumination optical system configured to illuminate illumination light toward a cornea and a light receiving optical system configured to receive reflection light from a cornea through a photodetector.

The illumination optical system and the light receiving optical system are placed in such a relation that respective optical axes are not coaxial and intersect with each other on the examinee's eye. For instance, the present device includes an optical system configured to irradiate light from an oblique direction to a cornea in a similar manner to a general specular microscope (a corneal endothelial cell imaging device) and receive reflection light from a cornea in a specular direction. The illumination optical system and the light receiving optical system are advantageous if they are placed symmetrically with respect to a certain central axis.

The present device is configured to asymmetrically limit the illumination light and the reflection light with respect to the optical axis, thereby ensuring brightness of an image and blocking the light that may adversely affect image formation (imaging). This improves the quality of a cornea image.

As a part for asymmetrically limiting reflection light, an asymmetric diaphragm, a lens holder having an asymmetric aperture, an asymmetric coating to an optical member, and others are adopted. The light-limiting part has only to be able to limit light and thus is advantageously a light shielding member capable of shielding light. As another example, an attenuating member for attenuating light (e.g., an optical member with a coating allowing 10% light transmission and 90% light shielding) may be used.

The asymmetric light-limiting part is provided in an optical path of the illumination optical system or the light receiving optical system. When the asymmetric light-limiting part is placed in the illumination optical system, the light-limiting part asymmetrically limits illumination light so that a component that may adversely affect image formation of reflection light from a cornea is limited in advance in an illumination optical path. On the other hand, when the asymmetric light-limiting part is placed in the light receiving optical system, the light-limiting part limits a part of reflection light from a cornea so that a component that may adversely affect image formation of the reflection light is limited in a light receiving optical path.

The asymmetric light-limiting part is advantageously placed near a condensing lens (an objective lens, a relay lens, an imaging lens, etc.) that acts to condense light. The asymmetric light-limiting part is also advantageously arranged between a plurality of lenses constituting a condensing optical system. In other words, it is advantageous that the asymmetric light-limiting part is placed in a position away from a condensing point (an image-forming point) of light. Such an arrangement enables uniformly limiting the light over a wide range of an observation area. In this case, the asymmetric light-limiting part has only to be arranged so as to provide the above advantages.

Advantageously, the asymmetric light-limiting part is configured to allow the light having passed through a central part of the objective lens in the light receiving optical system to travel toward the photodetector and also asymmetrically limit the light having passed through a peripheral part of the objective lens. Of the light having passed through the peripheral part of the objective lens (a region at a fixed distance away from the optical axis), the light passing on a side close to the central axis is allowed to pass through toward the photodetector, but the light passing on the opposite side is limited. This part is favorable when the light on the opposite side may adversely affect image formation due to aberration or the like. The light passing on the side close to the central axis contributes to image formation and thus both the imaging performance and securing image brightness can be achieved.

To asymmetrically limit the light having passed through the peripheral part of the objective lens in the light receiving optical system with respect to the optical axis, it is only necessary to avoid a part of the light from being received by the photodetector. Therefore, it is preferable to provide, in the optical path of the light receiving optical system, a part for limiting the light before passing through the objective lens or a part for limiting the light after passing through the objective lens but before being received by the photodetector. Of course, a part for limiting in advance the generation of reflection light that causes an adverse effect may be provided in the optical path of the illumination optical system so as to asymmetrically limit the light having passed through the peripheral part of the objective lens in the light receiving optical system.

In the event the light having passed through the central axis side of the peripheral part of the objective lens in the light receiving optical system is likely to adversely affect imaging due to aberration or the like, the asymmetricity of the asymmetric light-limiting part is preferably formed reversely.

The present device is preferably provided with an observation optical system for observing an anterior segment front image. It is advantageous to use an observation optical axis of this observation optical system as a central axis between the illumination optical system and the light receiving optical system arranged asymmetrically with each other. The illumination optical system and the light receiving optical system are preferably placed symmetrically right and left with respect to the observation optical axis. The asymmetric light-limiting part asymmetrically limits the reflection light from a cornea in a horizontal direction with respect to the optical axis of the light receiving optical system.

EXAMPLES

An example of the apparatus of the present embodiment will be concretely explained below, referring to drawings. FIG. 1 is an external side view of a configuration of a corneal imaging device of the present example.

A device 100 is a so-called floor-standing type apparatus, including a base table 1, a face support unit 2 attached to the base table 1, a movable unit 3 provided to be movable on the base table 1 by a sliding mechanism not shown, and a photographing part (a main unit) 4 provided to be movable with respect to the movable unit 3 and arranged to accommodate an imaging system and optical systems which will be described later.

The photographing part 4 is moved in right and left direction (X direction), up and down direction (Y direction), and front and back direction (Z direction) with respect to an examinee's eye E by a XYZ drive part 6 provided in the movable unit 3. The movable unit 3 is moved on the base table 1 in the XZ directions by operation of a joystick 5. When an examiner rotates a rotary knob 5a, the photographing part 4 is moved in the Y direction by Y-drive of by the XYZ drive part 6. At a top of the joystick 5, a start switch 5b is provided. A display monitor 95 is placed on an examiner side of the photographing part 4. In the present embodiment, the photographing part 4 is moved relative to the eye E by a sliding mechanism not shown or the XYZ drive part 6.

FIG. 2 is a schematic configuration diagram showing one example of optical arrangement of the optical systems contained in the photographing part 4 when seen from above and the configuration of a control system. FIG. 3 is a diagram of a first projection optical system and a second projection optical system seen from an examinee side. The whole configuration of the optical systems includes an illumination optical system 10 to irradiate illumination light from an illumination light source 12 toward a cornea Ec from an oblique direction, an imaging optical system (a light receiving optical system) 30 to receive reflection light from the cornea Ec including endothelial cells through a first imaging element 44 and obtain an endothelial cell image, a front projection optical system 50 to project alignment indices from front toward the center of the cornea Ec, first projection optical systems 60a and 60b to project infinite alignment indices toward the cornea Ec from oblique directions, second projection optical systems 65a to 65d (see FIG. 3) to respectively project finite alignment indices toward a peripheral portion of the cornea Ec from a plurality of oblique directions, an internal fixation optical system 70 to project a fixation target to the eye E from inside of the main unit, an anterior segment observation optical system 80 to observe an anterior segment image from front, and a Z alignment detecting optical system 85 to detect an alignment state of the photographing part 4 with respect to the eye E in the Z direction. Each concrete configuration of the above will be explained below.

The illumination optical system 10 includes an illumination light source (e.g., a visible LED, a flash lamp) 12 that emits visible light for photographing endothelium, a condensing lens 14, a slit plate 16, a dichroic mirror 18 that reflects visible light but transmits infrared light, and a light projection lens 20. Light emitted from the illumination light source 12 illuminates the slit plate 16 via the condensing lens 14. Slit light having passed through the slit plate 16 is then converged by the light projection lens 20 via the dichroic mirror 18, and irradiated to a cornea. Herein, the slit plate 16 and the cornea Ec are located in conjugated positions with respect to the light projection lens 20.

The imaging optical system 30 is symmetric right and left with the illumination optical system 10 with respect to an optical axis L1 and includes an objective lens 32, a dichroic mirror 34 that reflects visible light but transmits infrared light, a mask 35, a first image forming lens 36, a total reflection mirror 38, a second image forming lens 42, an asymmetric slit 43, a first two-dimensional imaging element (e.g., a two-dimensional CCD, CMOS, etc.) 44. The mask 35 is placed in a nearly conjugated position with the cornea Ec with respect to the objective lens 32. The first image forming lens (a relay lens) 36 and the second image forming lens (an imaging lens) 42 constitute an image-forming optical system to form an endothelial image on the imaging element 44. The imaging element 44 is placed in a nearly conjugated position with the cornea Ec with respect to a lens system of the imaging optical system 30.

<Configuration of Asymmetric Light-Limiting Means>

In FIG. 2, hatching H indicates the light which adversely affects image formation of an endothelial image, contributing to degradation in image quality. This light passes through a peripheral part of the objective lens 32 on an opposite side to a side close to the central axis (the optical axis L1).

FIG. 4 is a front view to explain the configuration of the asymmetric diaphragm 43. This asymmetric diaphragm 43 is a diaphragm to shield the light in right-and-left asymmetry, the light having been obtained by reflection of the light of the illumination optical system 10 at a cornea. The diaphragm 43 has an aperture portion 43a having a longitudinal direction in a horizontal direction and being asymmetric in the horizontal direction with respect to the optical axis L3, and a light shielding portion 43b formed outside the aperture portion 43a. The diaphragm 43 is placed so that the aperture portion 43a is eccentric in the horizontal direction with respect to the optical axis L3 of the light receiving optical system.

The aperture portion 43a allows the light in a central region including the optical axis L3 to path through toward the imaging element 44 and also allows a light part of the light in the peripheral region away from the optical axis L3, the light part being symmetric with a light part corresponding to the hatching H with respect to the optical axis L3, to pass through toward the imaging element 44.

The light shielding portion 43b includes a portion that shields the light part corresponding to the hatching H. This light shielding portion 43b blocks the light part of the hatching H and the light parts on upper and lower sides of the peripheral region away from the optical axis L3. Specifically, the asymmetric diaphragm 43 in FIG. 4 is also used as a light shielding portion that blocks the light parts having passed through the upper and lower regions in the light receiving optical system 30. The light shielding portion 43b may be a member providing a light attenuation action to allow part of light to pass therethrough.

The shape of the aperture portion 43a is not limited to a rectangular shape shown in FIG. 4 and is required only to be asymmetric in the horizontal direction with respect to the optical axis L3. For example, it may be a polygonal shape, a circular shape, an elliptical shape, or others.

Returning to FIG. 2. Corneal reflection light by the illumination optical system 10 travels in the optical axis L3 direction (an oblique direction) and is converged by the objective lens 32, thereafter reflected by the dichroic mirror 34, forming an image once by the mask 35 to intercept the light which may become noise at the time of obtaining an endothelial image. The light having passed through the mask 35 is imaged by the two-dimensional imaging element 44 via the first image forming lens 36, the total reflection mirror 38, the second image forming lens 42, and the asymmetric diaphragm 43. Accordingly, a corneal endothelial cell image with high resolution can be obtained. Output of the imaging element 44 is transmitted to a controller 90 and the obtained image is stored in a memory 92. Further, the cell image is displayed on a monitor 95.

The mask 35 shields noise light other than endothelial reflection light, while the asymmetric diaphragm 43 asymmetrically shields a part of the light from a corneal endothelium, the part including the light part corresponding to the hatching H and being likely to adversely affect image formation.

According to the asymmetric diaphragm 43 configured as above, allowing the light symmetric with the light part corresponding to the hatching H to be imaged on the imaging element 44 without blocking the light, it is possible to ensure brightness of an endothelial image. Further, the light part corresponding to the hatching H that may cause a decrease in imaging performance can be shielded, thereby removing the light including much aberration and thus achieving generation of a clear endothelial image with high resolution.

In FIG. 2, the asymmetric diaphragm 43 is placed between the second image forming lens 42 and the imaging element 44, but is not limited therein. For instance, the asymmetric diaphragm 43 is placed in an optical path of the imaging optical system 30 to limit reflection light from a cornea including light beams corresponding to the hatching H, while passing the light symmetric with the light part corresponding to the hatching H. To be concrete, the diaphragm 43 is placed between the cornea and the objective lens 32, between the objective lens and a first image-forming point (the mask 35), between the first image-forming point and the first image forming lens 36, or between the first image forming lens 36 and the second image forming lens 42. Of course, the size of the aperture portion 43a or the light shielding portion 43b is appropriately set according to a placement position of the asymmetric diaphragm 43.

As another configuration, the asymmetric diaphragm 43 is placed in an optical path of the illumination optical system 10 to limit illumination light to a cornea to thereby limit in advance the generation of reflection light from the cornea including light beams corresponding to the hatching H. To be more concrete, the asymmetric diaphragm 43 is disposed between the light source 12 and the slit plate 16, between the slit plate 16 and the light projection lens 20, or between the light projection lens 20 and a cornea.

The asymmetric diaphragm 43 is placed near the condensing lens (e.g., the objective lens 32, the first image forming lens 36, the second image forming lens 42, the light projection lens 20, the condensing lens 14) and thus can uniformly shield the light beams (hatching H), which may adversely affect image formation over the entire imaging region on a cornea. In a case where the condensing lens consists of a plurality of lenses, the diaphragm 43 may be placed in these lenses (e.g., between the first image forming lens 36 and the second image forming lens 42 in the image-forming optical system). Specifically, it is advantageous that the asymmetric diaphragm 43 is placed in a position away from the condensing point (the image-forming point) of light.

In contrast, when the diaphragm 43 is placed near the condensing point (the image-forming point) (near the mask 35 or the imaging element 44), light from each imaging region on a cornea is split. Therefore, of the light which adversely affects image formation, the light from a part of the imaging region can be shielded but the light from a remaining imaging region cannot be shielded. Even such a configuration can surely provide some advantages.

The front projection optical system 50 includes an infrared light source 51, a light projection lens 53, and a half mirror 55, and is configured to project infrared light for XY alignment detection from the observation optical axis L1 direction toward the cornea Ec. The infrared light emitted from the light source 51 is converted into parallel light by the light projection lens 53 and then reflected by the half mirror 55 to be projected onto the central portion of the cornea Ec, thereby forming an index i10 (see FIG. 5A).

The first projection optical systems 60a and 60b are in positions inclined at respective predetermined angles with respect to the optical axis L1. The first projection optical systems 60a and 60b respectively include infrared light sources 61a and 61b and collimator lenses 63a and 63b and are placed symmetrically right and left with respect to the optical axis L1 to project infinite indices to the eye E (see FIG. 2). The first projection optical systems 60a and 60b are placed on almost meridian lines nearly the same as the horizontal direction passing the optical axis L1 (see FIG. 3).

The lights emitted from the light sources 61a and 61b are respectively collimated by the collimator lenses 63a and 63b and then projected onto the cornea Ec, forming indices i20 and i30 (see FIG. 5B).

The second projection optical systems 65a to 65d are each arranged in positions inclined with respect to the optical axis L1. The second projection optical systems 65a to 65d respectively include infrared light sources 66a to 66d and are arranged symmetrically right and left with respect to the optical axis L1 to project finite indices to the eye E. The second projection optical systems 65a and 65b are placed above the optical axis L1 and at the same height (level) as each other in the Y direction. The second projection optical systems 65c and 65d are placed below the optical axis L1 and at the same height (level) as each other in the Y direction. Furthermore, the second projection optical systems 65a and 65b are respectively arranged symmetrically up and down with the second projection optical systems 65c and 65d with respect to the optical axis L1.

Herein, the lights from the light sources 66a and 66b are irradiated from oblique upper directions toward an upper portion of the cornea Ec, forming indices i40 and i50 which are virtual images of the light sources 66a and 66b. The lights from the light sources 66c and 66d are irradiated from oblique lower directions toward a lower portion of the cornea Ec, forming indices i60 and i70 which are virtual images of the light sources 66c and 66d (see FIGS. 5A and 5B).

According to the above index projection optical system, the index i10 is formed at a corneal apex of the eye E (see FIG. 5B). The indices i20 and i30 by the first projection optical systems 60a and 60b are formed at the same horizontal positions as the index i10 and symmetrically right and left with respect to the index i10. Further, the indices i40 and i50 by the second projection optical systems 65a and 65b are formed above the index i10 and symmetrically right and left with respect to the index i10. The indices i60 and i70 by the second projection optical systems 65c and 65d are formed below the index i10 and symmetrically right and left with respect to the index i10.

The internal fixation optical system 70 includes a visible light source (a fixation lamp) 71, a light projection lens 73, and a dichroic mirror 75 that reflects visible light and transmits infrared light. This optical system 70 is configured to project light onto the eye E in order to induce the eye E to hold fixation in a front direction. The visible light emitted from the light source 71 is converted into parallel light by the light projection lens 73 and then is reflected by the dichroic mirror 75, and projected onto a fundus of the eye E. An external fixation optical system not shown is further placed near the aforementioned first projection optical system and second projection optical system.

Returning to FIG. 2. The anterior segment observation optical system 80 includes an objective lens 82 and a two-dimensional imaging element 84 which is a second imaging element 84 to obtain an anterior segment front image, the system 80 being configured to image an anterior segment image and alignment indices through the second imaging element 84. As the two-dimensional imaging element 84, for example, there may be used a two-dimensional CCD image sensor (Charge coupled device image sensor) or a two-dimensional CMOS (Complementary Metal Oxide Semiconductor Image Sensor). Not limited to the above configurations, an optical-path coupling member for coupling an endothelium photographing optical path and an anterior segment observing optical path may be provided so that the first imaging element for imaging a corneal endothelium be used also as the second imaging element for capturing an anterior segment front image.

An anterior segment illuminated by an anterior segment illumination light source is imaged by the two-dimensional imaging element 84 via the dichroic mirror 75, the half mirror 55, and the objective lens 82. Similarly, a corneal reflection image by the front projection optical system 50, the first projection optical systems 60a and 60b, and the second projection optical systems 65a to 65d is received by the two-dimensional imaging element 84.

Output of the imaging element 84 is transmitted to the controller 90 and the anterior segment image imaged by the imaging element 84 is displayed on the monitor 95 as shown in FIGS. 5A and 5B. A reticle LT electronically displayed on the monitor 95 indicates a reference mark for XY alignment. The observation optical system 80 is used also as a detection optical system for detecting an alignment state (misalignment direction, deviation amount) of the photographing part 4 with respect to the eye E.

The Z alignment detection optical system 85 includes a light projecting optical system 85a for projecting detection light toward the cornea Ec from an oblique direction and a light receiving optical system 85b for receiving corneal reflection light by the light projecting optical system 85a. The optical axis L2 of the light projecting optical system 85a and the optical axis L3 of the light receiving optical system 85b are arranged in positions symmetric right and left with respect to the observation optical axis L1.

The light projecting optical system 85a includes an illumination light source 86 that emits infrared light, a condensing lens 87, a pin-hole plate 88, and the lens 20. Herein, the pin-hole plate 88 and the cornea Ec are disposed in nearly conjugated positions with respect to the lens 20. The light receiving optical system 85b includes for example the lens 32 and a one-dimensional light receiving element (a line sensor) 89. Herein, the one-dimensional light receiving element 89 and the cornea Ec are disposed in nearly conjugated positions with respect to the lens 32.

Infrared light emitted from the light source 86 illuminates the pin-hole plate 88 through the condensing lens 87. The light having passed through an aperture of the pin-hole plate 88 is projected onto the cornea Ec through the lens 20. Corneal reflection light of the light is received by the light receiving element 89 via the lens 32 and the dichroic mirror 34.

Output of the light receiving element 89 is transmitted to the controller 90 and will be utilized for detection of Z alignment with respect to the eye E. Herein, the position of alignment light to be received by the light receiving element 89 depends on a positional relationship between the photographing part 4 and the eye. E in the Z direction. For instance, the controller 90 detects the position of the corneal reflection light based on a detection signal from the light receiving element 89 and detects an alignment state in the Z direction. The alignment detection using the light receiving element 89 is utilized for precise alignment with respect to the eye E.

The controller 90 controls the entire device. The controller 90 is connected to the rotary knob 5a, the start switch 5b, the XYZ drive part 6, the two-dimensional imaging elements 44 and 84, each light source, the memory 92 serving as a storage means, and the monitor 95.

The embodiment is not limited to the aforementioned examples and may be variously modified or changed within the scope of design concept of a person skilled in the art.

REFERENCE SIGNS LIST

Figure 1:
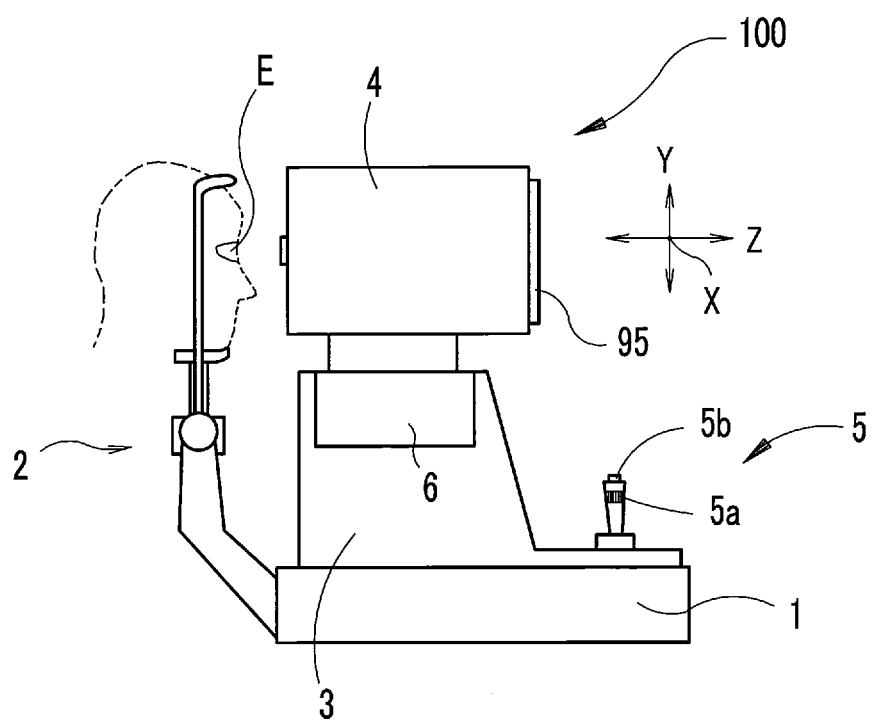
FIG. 1 is an external schematic view to explain an external appearance of a device of a present example.
Figure 2:
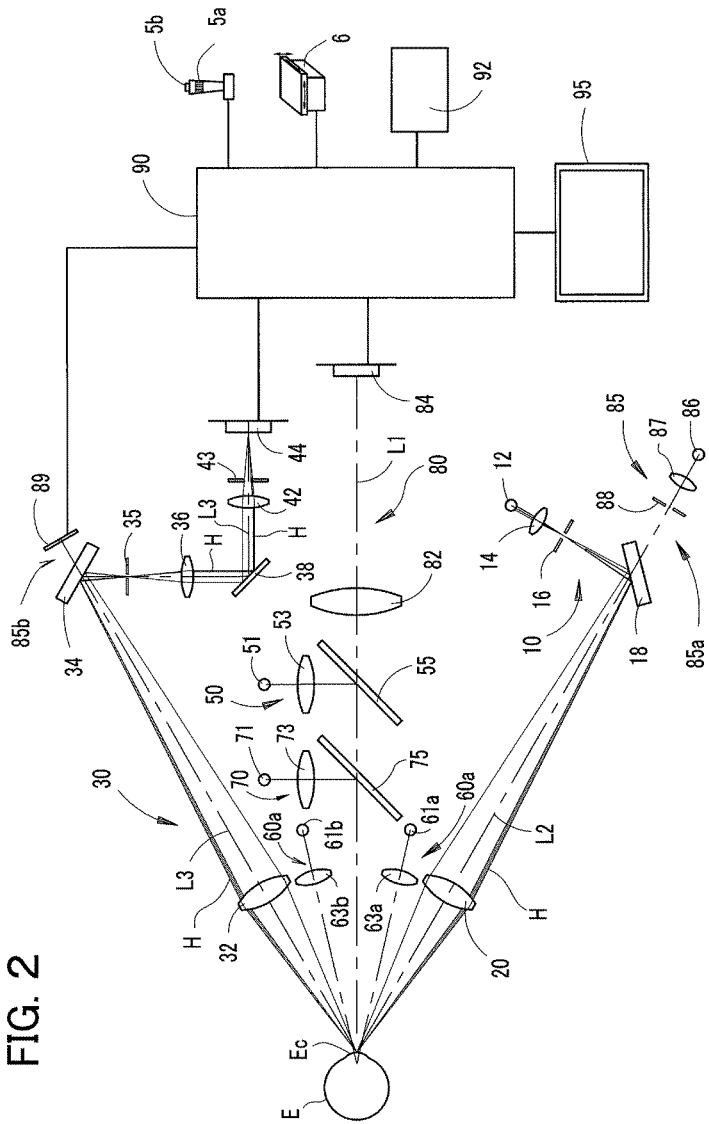
FIG. 2 is a schematic configuration view showing an example of optical arrangement of optical systems contained in a photographing part seen from above, and a configuration of a control system.
Figure 3:
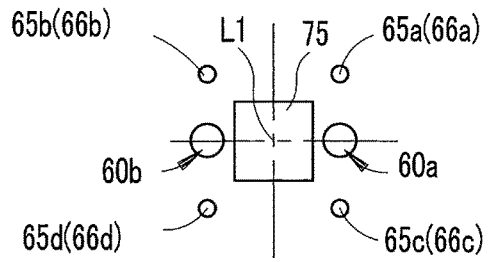
FIG. 3 is a diagram of a first projection optical system and a second projection optical system seen from a side of an examinee.
Figure 4:
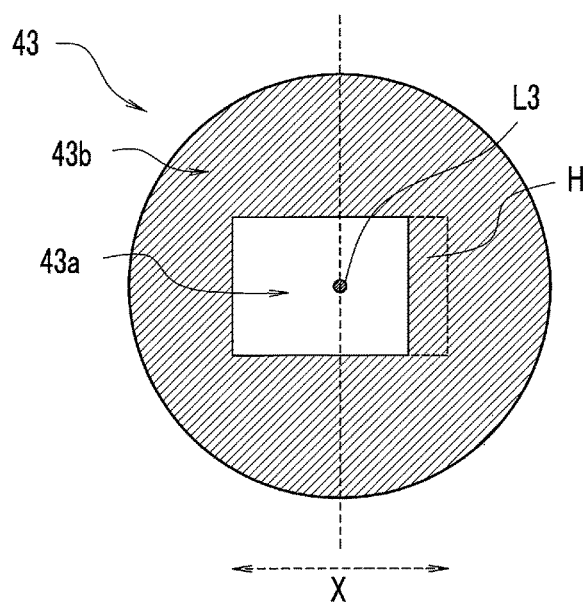
FIG. 4 is a front view to explain a configuration of an asymmetric diaphragm.
Figure 5A:
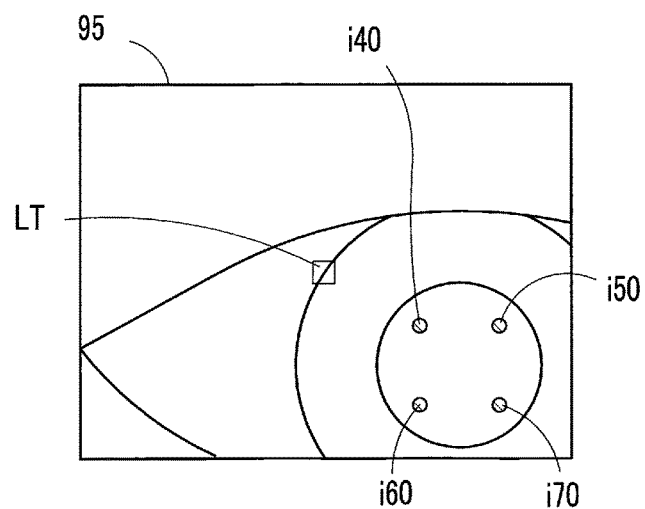
FIG. 5A is a diagram showing an example of an anterior segment observation screen when an endothelium of a cornea central portion is to be imaged and showing a display example of a misalignment state.
Figure 5B:
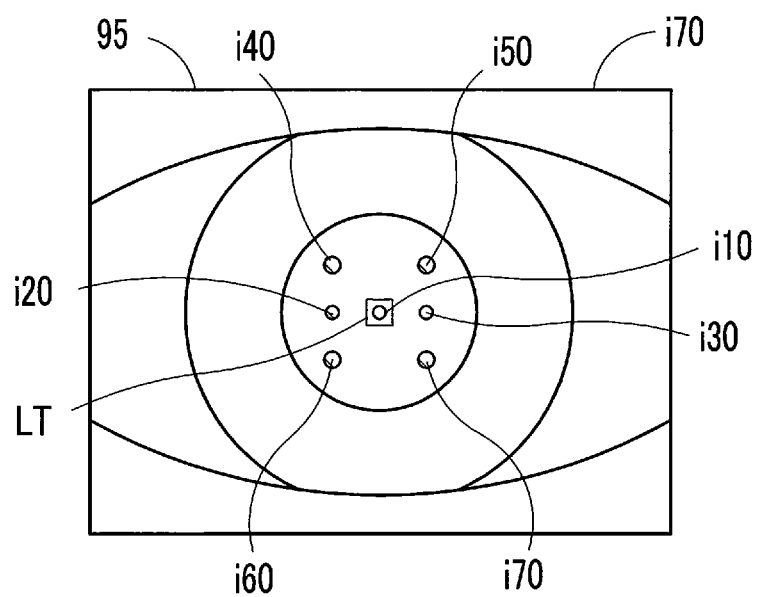
FIG. 5B is a diagram showing an example of an anterior segment observation screen when an endothelium of a cornea central portion is to be imaged and showing a display example of a proper alignment state.

4 Photographing part (Main unit)
6 Drive part
10 Illumination optical system
12 Illumination light source
30 Imaging optical system
43 Asymmetric slit
60a, 60b First projection optical system
65a to 65d Second projection optical system
80 Anterior segment observation optical system
85 Z alignment detection optical system
85a Light projecting optical system
85b Light receiving optical system
90 Controller
92 Memory
95 Monitor

The invention claimed is:

1. A corneal imaging device comprising:
an observation optical system configured to obtain an anterior segment front image of an eye, the observation optical system including an observation objective lens and an imager along a first optical axis; and
an optical system configured to photograph a corneal portion of the eye, the optical system including:
an illumination optical system configured to irradiate illumination light in a direction inclined with respect to the first optical axis toward a cornea; and
a light receiving optical system configured to receive reflection light from the cornea by a photodetector, the reflection light leaving the cornea at an inclined angle with respect to the first optical axis,
wherein the corneal imaging device includes a light-limiting part provided in an optical path of the optical system, the light-limiting part being configured to limit light asymmetrically with respect to a second optical axis of an optical path on which the light-limiting part is located,
the light-limiting part is placed in a position other than a condensing point of the light, and
the light-limiting part is configured to allow light having passed through a central part of an objective lens provided in the light receiving optical system to pass toward the photodetector, but asymmetrically limit light having passed through a peripheral part of the objective lens.

2. The corneal imaging device according to claim 1, wherein the optical system is configured to photograph endothelial cells of the cornea, the illumination optical system is configured to irradiate the illumination light to the cornea from an oblique direction, and the light receiving optical system is configured to receive the reflection light from the cornea in a specular direction at the cornea.

3. The corneal imaging device according to claim 1, further comprising an objective lens provided in the light receiving optical system, the objective lens having a central part and a peripheral part, wherein
the illumination optical system and the light receiving optical system are arranged symmetrically with respect to the first optical axis,
the light-limiting part is configured to:
allow the light having passed through the central part of the objective lens provided in the light receiving optical system to pass through toward the photodetector; and
allow a light part of the light having passed through the peripheral part of the objective lens on a side close to the first optical axis to pass through and limit a light part of the light having passed through the peripheral part of the objective lens on an opposite side to the first optical axis side.

4. The corneal imaging device according to claim 1, further comprising an objective lens provided in the light receiving optical system, the objective lens having a central part and a peripheral part, wherein
the illumination optical system and the light receiving optical system are arranged symmetrically with respect to the first optical axis,
the light-limiting part is configured to:
allow the light having passed through the central part of the objective lens provided in the light receiving optical system to pass through toward the photodetector; and
allow a light part of the light having passed through the peripheral part of the objective lens on an opposite side to a side close to the first optical axis to pass through and limit a light part of the light having passed through the peripheral part of the objective lens on the first optical axis side.

5. The corneal imaging device according to claim 1, wherein the illumination optical system and the light receiving optical system are arranged symmetrically with respect to the first optical axis.

6. The corneal imaging device according to claim 1, wherein the light-limiting part is placed in the light receiving optical system to asymmetrically limit the reflection light from the cornea.

7. The corneal imaging device according to claim 1, wherein the light-limiting part is placed in the illumination optical system to asymmetrically limit the illumination light.

8. The corneal imaging device according to claim 1, wherein the light-limiting part is provided with an aperture portion formed with an asymmetric aperture with respect to the second optical axis of the optical path and a light shielding portion formed outside the aperture portion.

9. The corneal imaging device according to claim 1, wherein the light-limiting part is one of an asymmetric diaphragm, a lens holder having an asymmetric opening, and an asymmetric coating to an optical member.

* * * * *